United States Patent
Putzer et al.

[19]

[11] Patent Number: 6,102,892
[45] Date of Patent: *Aug. 15, 2000

[54] DIAPER WITH PLEATS FOR CONTAINMENT OF LIQUID AND SOLID WASTE

[75] Inventors: Melissa C. Putzer, Oshkosh; Daniel R. Schlinz, Greenville, both of Wis.; Frank P. Abuto, Duluth, Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/886,950

[22] Filed: Jul. 2, 1997

Related U.S. Application Data

[63] Continuation of application No. 08/779,990, Dec. 23, 1996, abandoned.

[51] Int. Cl.[7] ................................................. A61F 13/15
[52] U.S. Cl. ............... 604/101; 604/385.16; 604/385.23; 604/385.25; 604/385.28; 604/385.29
[58] Field of Search .............................. 604/385.1, 385.2, 604/387, 397–402, 385.01, 385.101, 385.16, 385.19, 385.21, 385.23, 385.24, 385.25, 385.26, 385.27, 385.28, 385.3

[56] References Cited

U.S. PATENT DOCUMENTS

| | | |
|---|---|---|
| Re. 33,106 | 11/1989 | Beckestrom . |
| 1,676,144 | 7/1928 | Houseknecht . |
| 3,322,122 | 5/1967 | Daniel . |
| 3,776,233 | 12/1973 | Schaar . |
| 3,814,100 | 6/1974 | Nystrand et al. .................... 604/385.1 |
| 3,863,637 | 2/1975 | MacDonald et al. ................ 604/385.1 |
| 3,900,032 | 8/1975 | Heurlen ................................... 604/397 |
| 3,926,189 | 12/1975 | Taylor .................................... 604/397 |
| 3,929,134 | 12/1975 | Karami ................................. 604/385.1 |
| 3,943,930 | 3/1976 | Schaar . |
| 3,951,150 | 4/1976 | Schaar . |
| 3,978,861 | 9/1976 | Schaar . |
| 3,984,272 | 10/1976 | Teed . |
| 3,995,638 | 12/1976 | Schaar . |
| 3,995,640 | 12/1976 | Schaar . |
| 3,999,547 | 12/1976 | Hernandez . |
| 3,999,548 | 12/1976 | Hernandez . |
| 4,182,333 | 1/1980 | Schaar . |
| 4,246,900 | 1/1981 | Schroeder . |
| 4,413,996 | 11/1983 | Taylor . |
| 4,490,148 | 12/1984 | Beckestrom . |

(List continued on next page.)

FOREIGN PATENT DOCUMENTS

| | | |
|---|---|---|
| 0 585 904 | 3/1994 | European Pat. Off. . |
| 2 495 899 | 6/1982 | France . |
| 2 561 078 | 9/1985 | France . |
| 2 573 629 | 5/1986 | France . |
| 2349168 | 4/1974 | Germany ............................ 604/385.1 |
| 4018097 | 8/1991 | Germany ............................ 604/385.2 |
| 1246402 | 10/1989 | Japan . |
| 2142564 | 5/1990 | Japan . |
| 790062 | 2/1958 | United Kingdom . |
| 2 242 610 | 9/1991 | United Kingdom . |

Primary Examiner—John G. Weiss
Assistant Examiner—K. M. Reichle
Attorney, Agent, or Firm—Jeffrey B. Curtin

[57] ABSTRACT

An absorbent article is provided that is comfortable and suitable for absorbing and containing liquid and solid body exudates without leakage. The absorbent article may be a diaper that includes a backsheet layer, a substantially liquid-permeable liner layer, and an absorbent core located between the backsheet and the liner. The backsheet generally defines a front waistband section, a rear waistband section, and an intermediate section, with the intermediate section interconnecting the front and rear waistband sections and disposed between laterally opposed side margins. The backsheet layer has at least one pleat adjacent each side margin that defines an expanded volume when the pleat expands, the expanded volume being greater than the volume when the pleat is unexpanded. The pleat is accessible to body exudates that pass through or around the absorbent core.

26 Claims, 3 Drawing Sheets

U.S. PATENT DOCUMENTS

| | | |
|---|---|---|
| 4,501,587 | 2/1985 | Enloe . |
| 4,560,380 | 12/1985 | Tharel .................... 604/385.1 |
| 4,610,679 | 9/1986 | Matsushita . |
| 4,610,682 | 9/1986 | Kopp . |
| 4,623,342 | 11/1986 | Ito et al. ................ 604/385.2 |
| 4,662,877 | 5/1987 | Williams . |
| 4,681,579 | 7/1987 | Toussant et al. . |
| 4,731,065 | 3/1988 | Yamada . |
| 4,731,070 | 3/1988 | Koci . |
| 4,731,071 | 3/1988 | Pigneul . |
| 4,738,677 | 4/1988 | Foreman . |
| 4,753,645 | 6/1988 | Johnson . |
| 4,775,375 | 10/1988 | Aledo . |
| 4,778,459 | 10/1988 | Fuisz . |
| 4,781,711 | 11/1988 | Houghton et al. . |
| 4,781,713 | 11/1988 | Welch et al. . |
| 4,787,896 | 11/1988 | Houghton et al. . |
| 4,790,839 | 12/1988 | Ahr . |
| 4,795,454 | 1/1989 | Dragoo . |
| 4,816,025 | 3/1989 | Foreman . |
| 4,822,435 | 4/1989 | Igaue et al. . |
| 4,828,555 | 5/1989 | Hermansson . |
| 4,883,482 | 11/1989 | Gandrez et al. ............. 604/385.2 |
| 4,892,536 | 1/1990 | DesMarais et al. . |
| 4,904,251 | 2/1990 | Igaue et al. . |
| 4,938,755 | 7/1990 | Foreman . |
| 4,968,312 | 11/1990 | Khan . |
| 4,988,344 | 1/1991 | Reising et al. . |
| 4,988,345 | 1/1991 | Reising . |
| 4,990,147 | 2/1991 | Freeland . |
| 4,994,052 | 2/1991 | Kimura . |
| 5,021,051 | 6/1991 | Hiuke . |
| 5,062,840 | 11/1991 | Holt et al. . |
| 5,064,489 | 11/1991 | Ujimoto et al. . |
| 5,114,420 | 5/1992 | Igaue et al. . |
| 5,134,007 | 7/1992 | Reising et al. . |
| 5,171,236 | 12/1992 | Dreier et al. . |
| 5,176,672 | 1/1993 | Bruemmer et al. . |
| 5,207,662 | 5/1993 | James . |
| 5,211,641 | 5/1993 | Roos et al. . |
| 5,269,775 | 12/1993 | Freeland et al. . |
| 5,292,316 | 3/1994 | Suzuki . |
| 5,300,053 | 4/1994 | Genaro . |
| 5,330,459 | 7/1994 | Lavon et al. . |
| 5,334,177 | 8/1994 | Cohen . |
| 5,360,422 | 11/1994 | Brownlee et al. ............. 604/397 |
| 5,380,310 | 1/1995 | Mitrani .................... 604/385.1 |
| 5,417,680 | 5/1995 | Kimura et al. . |
| 5,425,729 | 6/1995 | Ishida et al. . |
| 5,451,442 | 9/1995 | Pieniak et al. . |
| 5,458,591 | 10/1995 | Roessler et al. . |
| 5,462,541 | 10/1995 | Bruemmer et al. . |
| 5,476,457 | 12/1995 | Roessler et al. . |
| 5,476,458 | 12/1995 | Glaug et al. . |
| 5,507,895 | 4/1996 | Suekane . |
| 5,527,303 | 6/1996 | Milby, Jr. et al. ............. 604/385.1 |
| 5,607,416 | 3/1997 | Yamamoto et al. ............. 604/397 |

…

DIAPER WITH PLEATS FOR CONTAINMENT OF LIQUID AND SOLID WASTE

This application is a continuation of Ser. No. 08/779,990 filed Dec. 23, 1996, abondoned.

The present invention relates to absorbent articles such as disposable diapers, and more particularly to absorbent articles that have a pleated backsheet to provide improved containment.

BACKGROUND OF THE INVENTION

Infants and other incontinent individuals wear absorbent articles such as diapers to receive and contain urine and other body exudates. Such articles are intended to prevent body exudates from soiling, wetting, or otherwise contaminating clothing or other articles, such as bedding, that come in contact with the wearer. The most common mode of failure for such products occurs when body exudates leak out of the gaps between the absorbent article and the wearer's leg or waist to adjacent clothing because they are not immediately absorbed within the article. This is most evident with loose fecal material, which is not easily absorbed by the absorbent article.

Several solutions to this problem have been proposed. For example, U.S. Pat. No. 4,490,148 describes an oblong absorbent body having lateral edge portions folded over to form side flaps. The edges of the side flaps contain elastic to contact the thigh creases of the crotch.

U.S. Pat. No. 5,527,303 shows an incontinent pad that has a backsheet with at least one pleat that is tacked with a soluble adhesive so that when the adhesive is wetted, the adhesive dissolves to allow the pleat to expand in conjunction with the absorbent core. A disadvantage to this absorbent article is that the liquid must first pass through the absorbent core before it enters the pleat, if at all. In addition, this absorbent article does not allow for the passage of solid matter into the pleat.

On the other hand, the present invention provides an absorbent article that has an expandable backsheet for collecting liquid and solid matter without it having to first pass through the absorbent core. Where the present invention is in the form of a diaper, a particular advantage is that the void volume of the diaper is increased at the outer surface of the diaper rather than internally, which does not increase the crotch width. Importantly, because the void volume is increased at the outer surface, the space between the wearer and the absorbent core increases with a concomitant reduction in discomfort to the wearer. In addition, the presence of pleats in accordance with the present invention allows the containment of both liquid and solid material without unduly increasing the overall bulk of the diaper.

SUMMARY OF THE INVENTION

The present invention provides a disposable absorbent article such as a diaper that is both thin and suitable for containing large volumes of liquid and solid body exudates without leakage. While the present invention will be particularly described in the form of a diaper, one of skill in the art will appreciate that it may be advantageously used with incontinent briefs, diaper holders, training pants, and the like. The diaper has a front waist region, a back waist region and an intermediate (or crotch) region that interconnects the front and back waist regions and is disposed between laterally opposed side margins. The diaper includes a liquid pervious liner suitable for contact with the wearer's body, a liquid impervious backsheet, and an absorbent core disposed between the liner and the backsheet. The liner may completely surround the absorbent core or may partially surround the portion of the absorbent core facing the wearer. In either case, the liner is preferably joined to the backsheet.

Each side or lateral margin defines a leg opening. In one embodiment, an elastic member is connected to each side or lateral margin of the diaper to provide elasticized leg openings. A containment flap may be associated with the elastic member and is suitably located inwardly or toward the central portion of the diaper to provide additional containment of body exudates.

The backsheet includes at least one pleat located adjacent and inwardly of each side margin such that the pleat defines an expanded volume when the pleat is expanded which is greater than the volume when the pleat is unexpanded. The pleat is accessible to fluid either by first passing through the absorbent core or by passing around the absorbent core. Preferably, each pleat extends substantially parallel to the longitudinal axis. More preferably, each pleat extends substantially the entire longitudinal distance from the front waist region to the rear waist region. In a particularly preferred embodiment, each pleat extends substantially the entire longitudinal distance from the front waist region to the rear waist region with the pleat being adhered in the front and rear waist regions and unadhered in the intermediate region.

DESCRIPTION OF THE PREFERRED EMBODIMENTS

Figure 1:
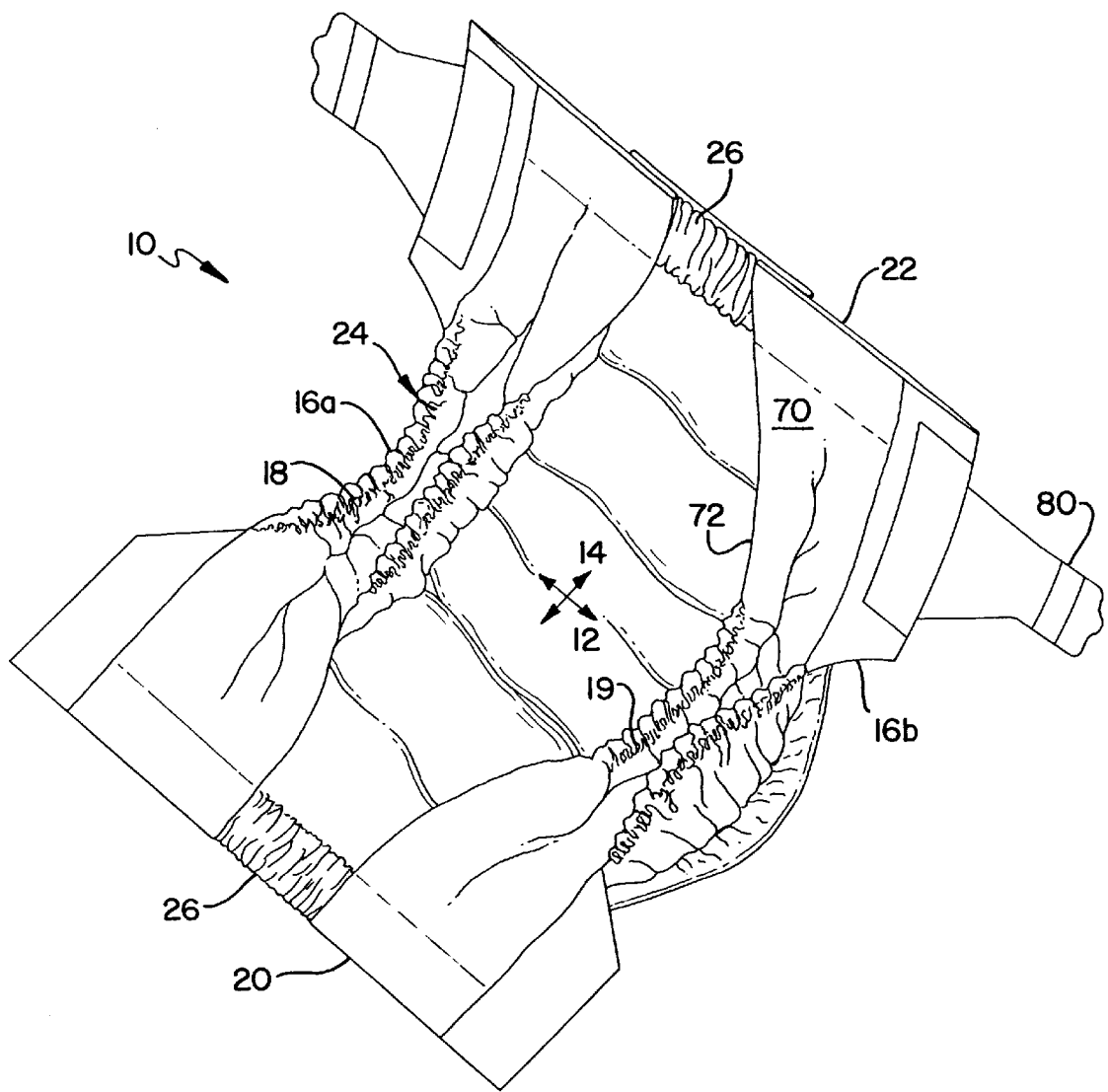
FIG. 1 is a perspective view of a diaper embodiment of the disposable absorbent article of the present invention with the surface of the diaper that contacts the wearer facing the viewer.

With reference to FIG. 1, an absorbent article, such as a diaper 10 is shown with the surface of the diaper that contacts the wearer facing the viewer. The diaper has a cross-wise, lateral axis or dimension 12 and a length-wise, longitudinal axis or dimension 14. The diaper 10 has laterally opposed side margins 16a, 16b, a front waistband region 20, a back waistband region 22, and an intermediate portion or crotch region 24 that interconnects the front and back waistbands and is laterally disposed between the side margins. The waistbands are arranged to encircle the front and back portions of the wearer's waist, and the intermediate portion is intended for placement between the wearer's legs. The waistbands may also have waist elastics 26.

The diaper comprises a substantially liquid-permeable liner 30, a liquid impervious backsheet layer 40, and an absorbent core 50 sandwiched between the liner and backsheet. The side margins define leg openings. In one embodiment, shown in FIG. 1, an elastic member 18 is provided in the region of each side margin to provide elasticized, gathered leg openings. A containment flap 19 may be associated with the elastic member. The liner, backsheet, absorbent structure, elastic members 18 and 26, and containment flaps 19 may be assembled in a variety of well-known diaper configurations. In accordance with the principles of the present invention, the backsheet is provided with at least one pleat adjacent each side margin.

The liner 30 presents a body-facing surface 32 which is compliant, soft-feeling, and non-irritating to the wearer's skin and a garment facing surface 34 associated with the absorbent structure. Preferably, the liner is sufficiently porous to be liquid permeable, permitting liquid to penetrate through its thickness. The liner is typically used to help isolate the wearer's skin from liquids held in the absorbent structure.

The liner fabrics may be composed of a substantially hydrophobic and substantially nonwettable material, and the hydrophobic material may optionally be treated with a surfactant or otherwise processed to impart a desired level of wettability and hydrophilicity. A suitable liner may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Various woven and nonwoven fabrics can be used for the liner. For example, the liner may be composed of a meltblown or spunbonded web of polyolefin fibers. The liner may also be a bonded-carded-web composed of natural and/or synthetic fibers.

An absorbent core, such as absorbent structure 50, is positioned between the liner 30 and backsheet 40 to form diaper 10. The absorbent core has a construction which is generally compressible, conformable, non-irritating to the wearer's skin, and capable of absorbing and retaining liquid body exudates. The absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

The absorbent structure may be manufactured in a wide variety of sizes and shapes (for example, rectangular, trapezoidal, T-shape, I-shape, hourglass shape, etc.) and from a wide variety of materials. Absorbent article structures suitable for use with the present invention are described in U.S. Pat. No. 5,192,606, the entire disclosure of which is hereby incorporated by reference in a manner that is consistent (not in contradiction) herewith. The size and the absorbent capacity of the absorbent structure should be compatible with the size of the intended wearer and the liquid loading imparted by the intended use of the absorbent article.

Various types of wettable, hydrophilic fibrous material can be used to form the component parts of the absorbent structure. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made form inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The entire absorbent structure or any individual portion thereof, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to the absorbent structure and to other components of the product construction.

The backsheet 40 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. The backsheet can help prevent the exudates contained in the absorbent structure from wetting articles such as bedsheets and overgarments which contact the diaper.

The backsheet may optionally be composed of a microporous, "breathable" material which permits vapors to escape from the absorbent structure while still preventing liquid exudates from passing through the backsheet. For example, the breathable backsheet may be composed of a microporous polymer film a nonwoven fabric which has been coated or otherwise treated to impart a desired level of liquid impermeability.

The size of the backsheet is typically determined by the size of the absorbent structure and the exact diaper design selected. The backsheet, for example, may have a generally T-shape, a generally I-shape or a modified hourglass shape, and may extend beyond the terminal edges of the absorbent structure by a selected distance. Preferably, the backsheet has an hourglass shape.

The liner and backsheet may be generally coextensive, and may have a length and width dimension that are generally larger than the corresponding dimensions of the absorbent structure. Alternatively, the liner may simply surround the absorbent structure while the backsheet has a length and width dimension larger than the corresponding dimensions of the absorbent structure.

Figure 2:
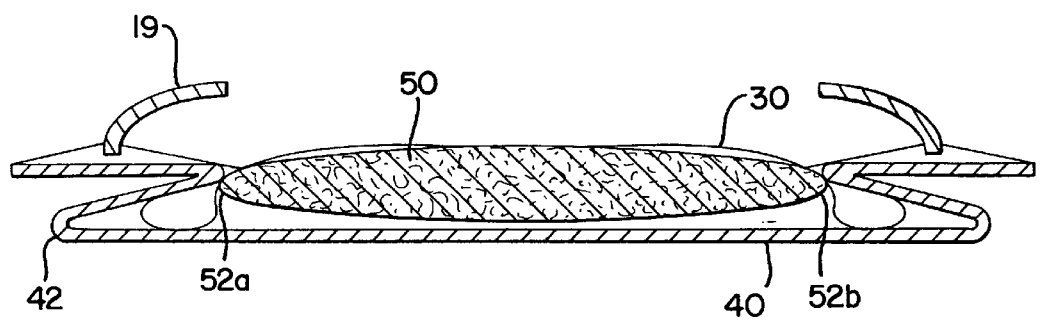
FIG. 2 is a cross sectional view of one embodiment of the article of FIG. 1 showing the pleat in a folded or closed state. In this embodiment, the liner partially surrounds the portion of the absorbent core facing the wearer's body and the absorbent core is located in the central portion of the diaper between the pleats.

The liner 30 and backsheet 40 are connected or otherwise associated together in an operable manner. As used herein, the term "associated" encompasses configurations in which the liner is directly joined to the backsheet by affixing the liner directly to the backsheet and configurations wherein the liner is joined to the backsheet by affixing the liner to intermediate members which in turn are affixed to the backsheet. As best seen in FIG. 2, the liner and backsheet can be affixed directly to each other at the diaper periphery by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix the liner to the backsheet.

It should be readily appreciated that the above-described attachment means may also be employed to interconnect and assemble together the various other component parts of the article described herein.

Figure 6:
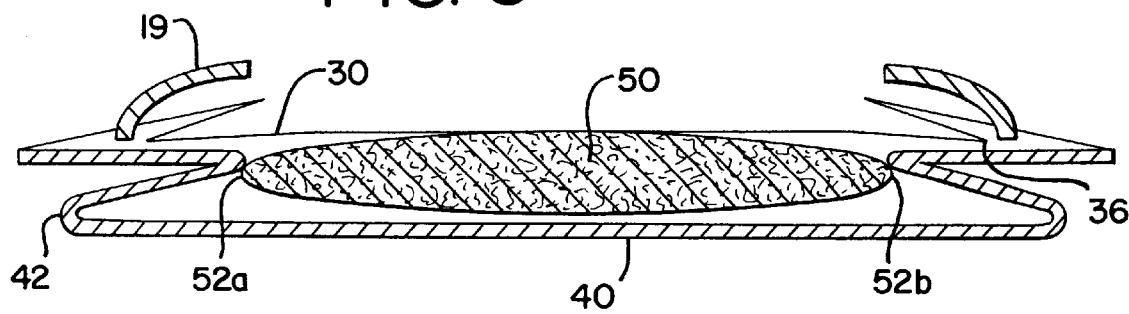
FIG. 6 is a cross sectional view of another embodiment of the article of the present invention showing the pleat in the closed state. This embodiment is similar to that shown in FIG. 2 except that the liner does not extend into the pleat formed in the backsheet until the pleat is in the open or expanded state.

In one embodiment of the present invention best seen in FIG. 2, the liner 30 is disposed and secured in facing relation with the backsheet layer 40. The marginal side regions of the liner are operably connected to corresponding marginal side regions of the backsheet layer. Each of the attached marginal side regions of the liner and backsheet layers is located laterally outboard of the associated side edge region of the absorbent structure. In this embodiment, the liner partially surrounds the uppermost portion of the absorbent structure, i.e., the portion of the absorbent structure facing the wearer. In addition, in this embodiment, the liner contains a pleat 36 that extends into the pleat 42 formed in the backsheet. Alternatively, as shown in FIG. 6, the liner partially surrounds the uppermost portion of the absorbent structure but the liner pleat 36 does not extend into the backsheet pleat 42 when the pleat 42 is unexpanded. When the pleat 42 expands, the liner pleat 36 will assume the configuration shown in FIG. 2. Preferably in these embodiments, the side edges of the absorbent structure 52a, 52b do not extend laterally beyond the innermost portion of the pleat formed in the backsheet.

In addition, in this embodiment where the absorbent structure does not extend beyond the innermost portion of the pleat, filler material (not shown) may be incorporated in the pleated area sandwiched between the liner and the backsheet. The filler material may include tissue, wicking material, super-absorbent or chemical material that can absorb and/or mix with the body exudate to absorb, eliminate odor, or neutralize the body exudates.

Figure 4:
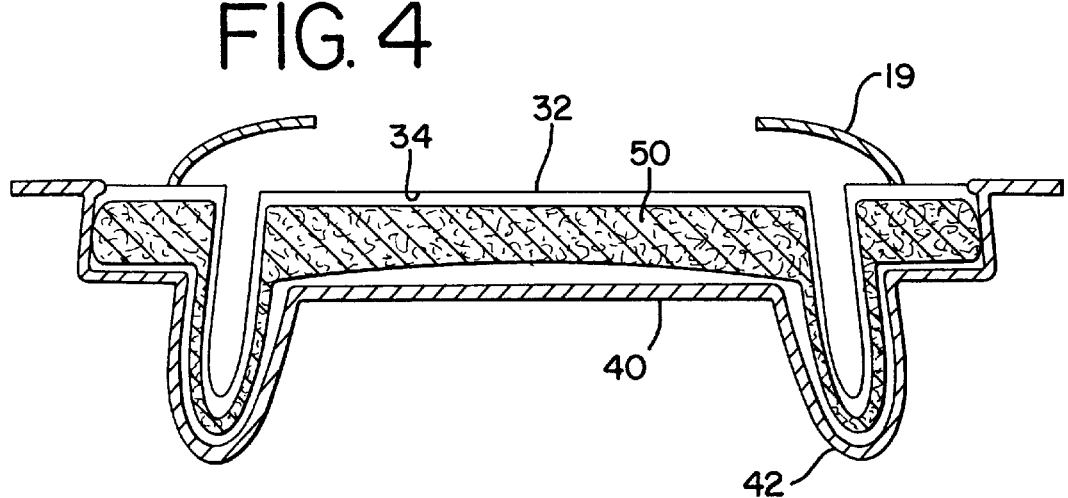
FIG. 4 is a cross sectional view of another embodiment of the article of the present invention showing the pleat in an open or expanded state. In this embodiment the absorbent structure extends substantially the entire lateral dimension of the diaper.

In another similar embodiment as best shown in FIG. 4, the side edges of the absorbent structure may extend substantially from one side margin to the other side margin either along the entire longitudinal length of the diaper or only in the front and back waistband regions. In either case, it may be preferable if the absorbent structure has a smaller thickness in the area between the innermost portion of the pleat and the outermost portion of the pleat so that the bulk of the diaper is not unduly increased.

Figure 5:
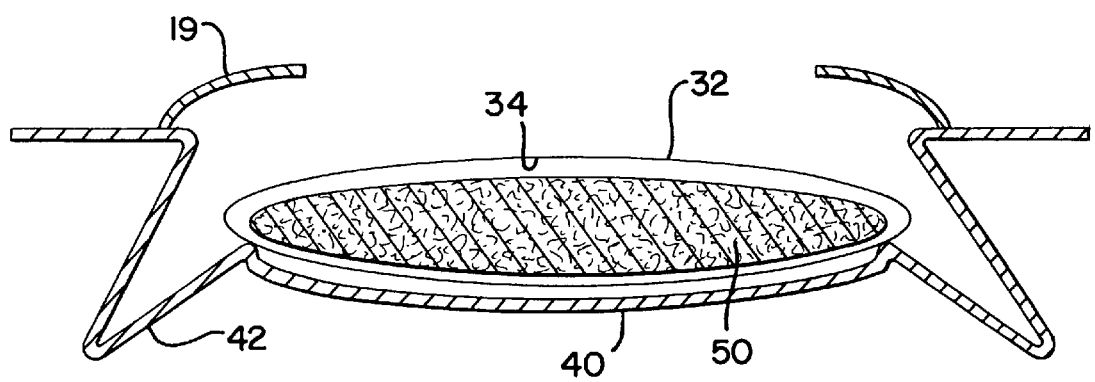
FIG. 5 is a cross sectional view of another embodiment of the article of the present invention showing the pleat in an open or expanded state. In this embodiment, the liner completely surrounds the absorbent core.

Alternatively, in another embodiment of the present invention best seen in FIG. 5, the liner completely surrounds the absorbent structure. The absorbent core illusrated in FIG. 5 has an unfolded cross section. In this embodiment, the liner is preferably associated with or joined to the backsheet. More preferably the liner is associated with the backsheet only in the area between the innermost portion of the pleats.

Figure 3:
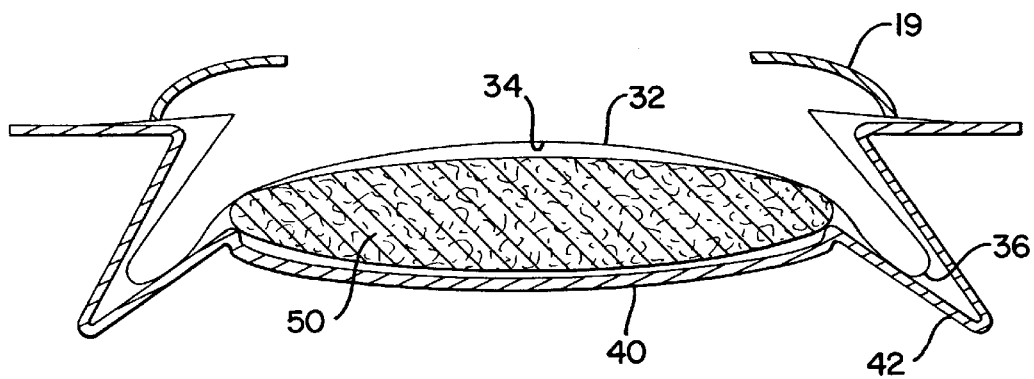
FIG. 3 is a cross sectional view of one embodiment of the article of FIG. 2 showing the pleat in an open or expanded state.

In accordance with the principles of the present invention and as will be more fully explained below, it is to be understood that in each of the above embodiments body exudates may access the pleats directly (by passing around the absorbent structure) or indirectly (by passing through the absorbent structure). At least one pleat 42 is provided in the backsheet adjacent each side margin. Alternatively, a plurality of pleats may be provided adjacent each side margin. Preferably, the pleats extend in a direction substantially parallel to the longitudinal axis of the diaper along the entire length or a portion of the length of the diaper. More preferably, the pleats extend along the entire length of the diaper. In this instance, the portion of the pleats located in the front and back waistband region are tacked or adhered so that they do not open, while in the intermediate or crotch region the pleats are unadhered. Thus, the pleats allow the backsheet to expand away from the wearer's body surface in the crotch region while maintaining a close fit in the front and back waistband regions and preventing any leakage in those areas. As can be seen in FIGS. 2 and 3, the illustrated pleats expand in a direction away from the user.

Preferably, the pleat is located inwardly of the side margin and thus the elastic member. By providing the pleat in this location, the liquid and solid body exudates need not first pass through the absorbent structure before settling within the expanded volume defined by the expanded pleat. Referring to FIGS. 3 and 5, it will be appreciated that the body exudates may have a flow path through or around the absorbent structure.

The pleat may be formed in any suitable manner. For example, the liner and backsheet can be pre-pleated with folding boards using a machine or by hand. In this method, the diaper will assume a configuration substantially similar to that shown in FIG. 6. Another method of forming pleats can include providing slits in the forming wire upon which the backsheet lies during processing. Thus, after the absorbent structure and liner have been placed onto the backsheet, a pushing object such as a knife can push the liner and backsheet through the slit to provide a diaper having a configuration substantially similar to that shown in FIG. 4. In yet another method, the liner and backsheet may be pleated after the absorbent core has been sandwiched by the liner and backsheet to obtain a diaper configuration shown in FIG. 2. Of course, other methods of providing pleats will be known to those of skill in the art.

In a preferred embodiment, an elastic member 18 is disposed along each of the longitudinal side edges 16a, 16b of the diaper. The elastic member 18 can be connected to either or both of the liner and backsheet layers to provide elasticized side margins of the diaper article, and can be arranged to draw and hold diaper 10 against the legs of the wearer. No matter where the elastic member is connected, it should be appreciated that in the intermediate region, the elastic member should be connected outwardly of the outermost portion of the pleat so that the pleat can fully expand. Waist elastic members 26 may also be disposed adjacent either or both of the end edges of diaper 10 to provide elasticized waistbands.

Preferably, the elastic members 18 and 26 are secured to the diaper in an elastically contractible condition so that in a normal, under strain configuration, the elastic members effectively contract against the diaper. For example, the elastic members may be stretched and secured while the diaper is in an uncontracted condition. Alternatively, the diaper may be contracted, for example, by pleating, and the elastic members secured and connected to the diaper while the elastic members are in their unrelaxed or unstretched condition. Still other means, such as heat-shrink elastic material, may be used to gather and shrink the garment.

The elastic members 18 may extend the entire length of the backsheet. Alternatively, the elastic members may extend essentially along the complete length of crotch region 24 or any other length suitable providing the arrangement of elastically contractible lines desired for the particular diaper design.

Elastic members 18 and 26 may have any of a multitude of configurations. For example, the width of the individual elastic members 18 may be varied from 0.25 millimeters (0.01 inches) to 25 millimeters (1.0 inches) or more. The elastic members may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to the diaper with sprayed or swirled patterns of hot melt or other type of adhesive.

In the illustrated embodiments of the invention, the elastic member comprises a carrier sheet 70 to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer available from DuPont. Each elastic strand is typically within the range of about 620–1050 decitex (dtx). In addition, the elastic strands may be generally straight or optionally curved.

As noted above, the diaper can include elasticized containment flaps associated with or connected to either or both of the liner and backsheet to provide an elasticized containment. As with the elastic member, the containment flap should, at least in the intermediate region, be connected outwardly of the outermost portion of the pleat so that the pleat can fully expand. In one embodiment, as shown in FIG. 1, the flaps 19 are provided as part of a side carrier 70. The containment flaps are located inboard the elastic members 18. The containment flaps may be constructed of a fibrous material which is similar to the material comprising the liner. Other conventional materials, such as polymer films, may also be used. In other aspects of the invention, the flaps are constructed of a material which is permeable to gas, such as ambient air. Alternative configurations of the invention can include barrier flaps which are constructed of a material which is resistant to a passage of aqueous liquid, such as urine, therethrough. For example, the flaps may be constructed of a spunbond-meltblown-spunbond (SMS) laminate material.

Each containment flap includes a movable edge region 72 that can include one or more individual strands of elastomeric material. For example, a plurality of elastic strands may be configured in a spatially separated, generally parallel arrangement, and a suitable elastic strand can, for example, be composed of a LYCRA elastomer. The elastic is preferably connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of liner 32 toward a generally upright and approximately perpendicular configuration, especially in the crotch section of the diaper. By providing a generally upright and approximately perpendicular configuration, the flap operates in conjunction with the above-described pleats to provide a volume for the containment of liquid and solid body exudates.

Fastening means, such as tape tab fasteners 80, are typically applied to the back waistband region 22 of diaper 10 to provide a mechanism for holding the diaper on the wearer. Tape tab fasteners 80 can be any of those well known in the art, and are typically applied to the corners of diaper 10. For example, adhesive fasteners, mechanical fasteners, hook and loop fasteners, snaps, pins or buckles, may be used alone, or in combination. In the shown configuration, the fasteners are the male or hook portion of a hook-and-loop fastener, which are constructed to releasably adhere to a landing zone patch (not shown) attached to the front waistband section of the diaper to provide a refastenable fastening system. In the shown configuration, the landing zone patch comprises the female or loop portion of a hook-and-loop fastener.

It should be understood that a wide range of changes and modifications can be made to the embodiments described above. It is therefore intended that the foregoing description illustrates rather than limits this invention and that it is the following claims, including all equivalents, which define this invention.

What is claimed is:

1. A disposable absorbent article having a longitudinal axis and a transverse axis, a front waistband region, a back waistband region, and an intermediate region interconnecting the front and back waistband regions and disposed between laterally opposed side margins, the article further comprising:
   a. a liquid pervious liner;
   b. a liquid impervious backsheet;
   c. an absorbent core disposed between the liner and the backsheet, the absorbent core having an unfolded lateral cross-section and a first lateral side edge and a second lateral side edge; and
   d. at least one pleat adjacent each side margin that is unadhered in the intermediate region, wherein the at least one pleats allow the backsheet to expand outwardly away from a wearer's body surface in the intermediate region and define an expanded article void volume when the at least one pleats expand which is greater than the article void volume when the at least one pleats are unexpanded and wherein the at least one pleats are disposed laterally outward of the first and second lateral side edges of the absorbent core.

2. The disposable absorbent article of claim 1 wherein the at least one pleats extend in a direction substantially parallel to the longitudinal axis.

3. The disposable absorbent article of claim 2 wherein the at least one pleats extend substantially from the front waistband region to the back waistband region.

4. The disposable absorbent article of claim 3 wherein the at least one pleats are adhered in the front and rear waistband regions.

5. The disposable absorbent article of claim 1 wherein the backsheet includes a plurality of pleats.

6. The disposable absorbent article of claim 5 wherein the pleats extend in a direction substantially parallel to the longitudinal axis.

7. The disposable absorbent article of claim 1 further comprising a containment flap spaced inwardly from each side margin.

8. The disposable absorbent article of claim 1 wherein the liner extends transversely to each side margin.

9. The disposable absorbent article of claim 1 wherein the liner completely surrounds the absorbent core.

10. The disposable absorbent article of claim 1 further comprising an elastic member connected to each side margin to provide elasticized leg openings.

11. The disposable absorbent article of claim 1 wherein the at least one pleats are formed on the backsheet.

12. The disposable absorbent article of claim 11 further comprising at least one pleat formed on the liner.

13. The disposable absorbent article of claim 11 wherein when the article is placed on a user, the pleats expand in a direction away from the user.

14. A disposable absorbent article having a longitudinal axis and a transverse axis, a front waistband region, a back waistband region, and an intermediate region interconnecting the front and back waistband regions and disposed between laterally opposed side margins, the article further comprising:

a. a liquid pervious liner;
   b. a liquid impervious backsheet;
   c. an absorbent core disposed between the liner and the backsheet;
   d. at least one pleat adjacent each side margin wherein the at least one pleats allow the backsheet to expand outwardly away from a wearer's body surface in the intermediate region and define an expanded article void volume when the at least one pleats expand which is greater than the article void volume when the at least one pleats are unexpanded and wherein the at least one pleats extend in a direction substantially parallel to the longitudinal axis from the front waistband to the back waistband region and are adhered in the front and rear waistband regions and unadhered in the intermediate region; and
   e. a containment flap spaced inwardly from each side margin.

15. The disposable absorbent article of claim 14 further comprising an elastic member connected to each side margin to provide elasticized leg openings.

16. The disposable absorbent article of claim 15 wherein the backsheet includes a plurality of pleats.

17. The disposable absorbent article of claim 16 wherein each of the pleats extend in a direction substantially parallel to the longitudinal axis.

18. The disposable absorbent article of claim 14 wherein the liner completely surrounds the absorbent core.

19. The disposable absorbent article of claim 18 wherein the liner is associated with the backsheet only in an area laterally inward of the at least one pleats.

20. The disposable absorbent article of claim 14 wherein the absorbent core has a first lateral side edge and a second lateral side edge and the at least one pleats are located laterally outwardly from the lateral side edges.

21. A disposable absorbent article having a longitudinal axis and a transverse axis, a front waistband region, a back waistband region, and an intermediate region interconnecting the front and back waistband regions and disposed between laterally opposed side margins, the article further comprising:

a. a liquid pervious liner;
   b. a liquid impervious backsheet;
   c. an absorbent core disposed between the liner and the backsheet, wherein the liner completely surrounds the core; and
   d. at least one pleat adjacent each side margin, wherein the at least one pleats allow the backsheet to expand outwardly away from a wearer's body surface in the intermediate region and define an expanded article void volume when the at least one pleats expand which is greater than the article void volume when the at least one pleats are unexpanded and wherein the at least one pleats extend in a direction substantially parallel to the longitudinal axis from the front waistband to the back waistband region and are adhered in the front and rear waistband regions and unadhered in the intermediate region.

22. The disposable absorbent article of claim 21 wherein the absorbent core has a first lateral side edge and a second lateral side edge and the at least one pleats are located laterally outwardly from the lateral side edges.

23. A disposable absorbent article having a longitudinal axis and a transverse axis, a front waistband region, a back waistband region, and an intermediate region interconnecting the front and back waistband regions and disposed between laterally opposed side margins, the article further comprising:

a. a liquid pervious liner;
   b. a liquid impervious backsheet having at least one pleat adjacent each side margin wherein the at least one pleats allow the backsheet to expand outwardly away from a wearer's body surface in the intermediate region and define an expanded article void volume when the at least one pleats expand which is greater than the article void volume when the at least one pleats are unexpanded, wherein the at least one pleats extend in a direction substantially parallel to the longitudinal axis from the front waistband region to the back waistband region and are adhered in the front and rear waistband regions and unadhered in the intermediate region; the liner being associated with the backsheet only in an area laterally inward of the at least one pleats; and
   c. an absorbent core disposed between the liner and the backsheet and having an unfolded lateral cross-section and a first lateral side edge and a second lateral side edge, wherein the liner completely surrounds the core and the at least one pleats are disposed laterally outward of the first and second lateral side edges.

24. A disposable absorbent article having a longitudinal axis and a transverse axis, a front waistband region, a back waistband region, and an intermediate region interconnecting the front and back waistband regions and disposed between laterally opposed side margins, the article further comprising:

a liquid pervious liner defining an exposed inner surface of the absorbent article;
   a liquid impervious backsheet, the backsheet having a greater lateral width than the liner;

an absorbent core disposed between the liner and the backsheet, the absorbent core having longitudinally extending outer edges disposed inwardly of the side margins; and a pleat disposed between the side margin and the absorbent core outer edge on each lateral side of the absorbent article, each of the pleats disposed laterally outward of the liner wherein each of the pleats allows the backsheet to expand outwardly away from a wearer's body surface in the intermediate region thereby defining an expanded article void volume when each of the pleats expands which is greater than the article void volume when each of the pleats is unexpanded.

25. The disposable absorbent article of claim 24 wherein the liner completely encircles the absorbent core.

26. The disposable absorbent article of claim 24 wherein the liner is attached to the backsheet at a location between the pleats.

* * * * *